Figure 1:
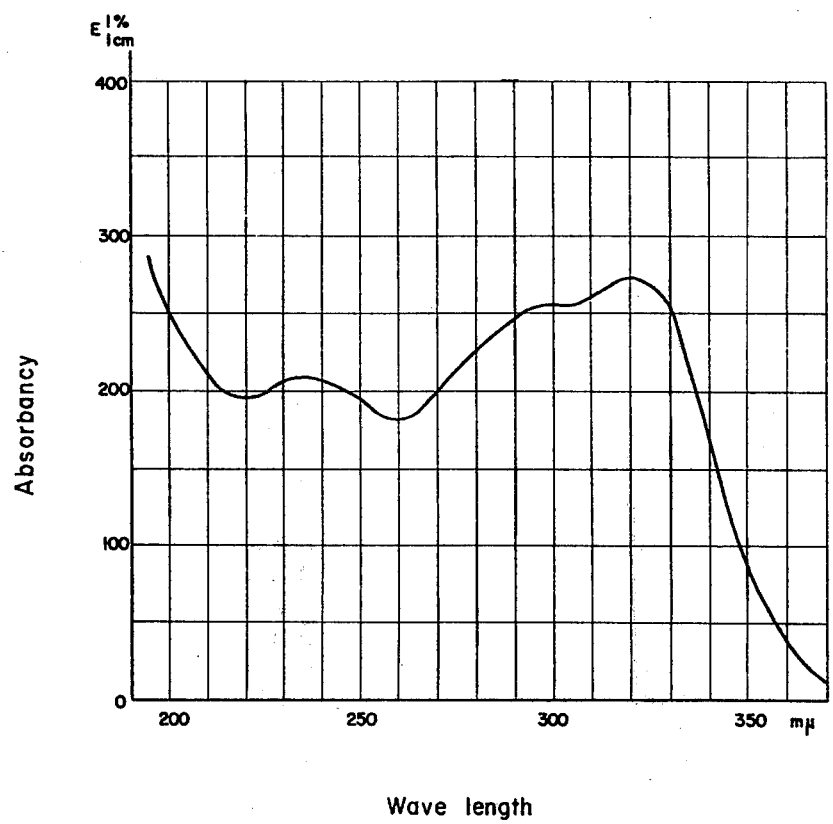

United States Patent [19]

Hasegawa et al.

[11] 4,017,485
[45] Apr. 12, 1977

[54] 7-METHOXYCEPHALOSPORIN DERIVATIVES

[75] Inventors: Tōru Hasegawa, Kawanishi; Kazunori Hatano; Hiroshi Fukase, both of Osaka; Hidesuke Iwasaki, Itami, all of Japan

[73] Assignee: Takeda Chemical Industries, Ltd., Osaka, Japan

[22] Filed: Sept. 11, 1974

[21] Appl. No.: 505,089

[30] Foreign Application Priority Data

Sept. 18, 1973 Japan ............................ 48-105287

[52] U.S. Cl. ........................ 260/240 J; 260/243 C; 424/246; 195/80 R
[51] Int. Cl.² ....................................... C07D 501/20
[58] Field of Search ................................ 260/243 C

[56] References Cited

UNITED STATES PATENTS

| | | | |
|---|---|---|---|
| 3,718,644 | 2/1973 | Weston et al. | 260/243 C |
| 3,855,213 | 12/1974 | Dunn et al. | 260/243 C |
| 3,867,380 | 2/1975 | Dunn et al. | 260/243 C |

*Primary Examiner*—Nicholas S. Rizzo
*Attorney, Agent, or Firm*—Wenderoth, Lind & Ponack

[57] ABSTRACT

A novel antibiotic C-2801-X represented by the formula

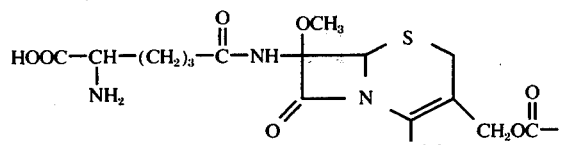
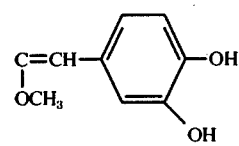

is produced by cultivating a microorganism of the genus Streptomyces. The compound is useful in the treatment of mammals, including human beings, suffering from urinary tract infections, respiratory tract infections, colitis, septicema, purulent diseases, etc.

1 Claim, 2 Drawing Figures

7-METHOXYCEPHALOSPORIN DERIVATIVES

This invention relates to a novel antibiotic C-2801-X, and the production of the same.

It has been found by the present inventors that a novel antibiotic is produced by a microorganism belonging to the genus Streptomyces and is accumulated in the culture broth; that the new antibiotic has cephalosporin-type chemical structure and is useful, e.g., in the treatment of mammals including human beings suffering from urinary tract infections, respiratory tract infections, colitis, septicema, purulent diseases, etc. The new antibiotic has been named "Antibiotic C-2801-X."

It is the principle object of the present invention to provide the novel antibiotic C-2801-X and its pharmaceutically acceptable salts.

Another object of the present invention is to provide an industrially advantageous process for producing the said antibiotic C-2801-X.

A further object is to provide the means for recovering the product Antibiotic C-2801-X.

Other objects will be made apparent from the description and claims hereinafter.

Said objects are realized by cultivating a C-2801-X-producing microorganism of the genus Streptomyces in a suitable culture medium containing assimiliable carbon source and digestible nitrogen source until the antibiotic is substantially accumulated in the culture broth, and recovering said antibiotic C-2801-X therefrom.

The microorganisms to be employed for the purpose of this invention can be isolated from natural sources and also obtained from type culture collections. These microorganisms include, for example, *Streptomyces heteromorphus* C-2801 which has been isolated from a soil sample obtained in Cabanatuan City of the Republic of the Philippines and *Streptomyces panayensis* C-2878 and *Streptomyces panayensis* C-2879 which have been isolated from soil samples collected in Panay Island of the Republic of the Philippines.

Hereafter *Streptomyces heteromorphus* C-2801, *Streptomyces panayensis* C-2878 and *Streptomyces panayensis* C-2879 are sometimes referred to briefly as Strain C-2801, and Strain C-2878 and Strain C-2879, respectively.

The microobiological characteristics and cultural characteristics of Strain C-2801 as isolated by our screening are as follows. Unless otherwise indicated, the cultural characteristics are those observed in the routine manner after 14 days of cultivation at 28° C.

1. Morphology (on glucose asparagine agar)

An aerial mycelium, about 1 $\mu$, extends far from the well branched vegetative mycelium, with short monopodially extending branches. The tip of the aerial mycelium carries chains of spores of varied configurations such as looped, hooked, wavy, incomplete-spiral, open-spiral and closed-spiral. True whorls representative of verticillate cultures are not observed. The number of spores per chain varies from a few to more than 10. Each spore is ellipsoidal, oval or cylindrical (0.6 – 0.7 × 0.8 – 1.2 $\mu$), with a spiny suface. No other special organs are observed.

2. Cultural characteristics

1. Sucrose nitrate agar
Growth: moderate, light tan to grayish brown.
Aerial mycelium: white to cream.
Reverse: dark tan to dark brown.
Soluble pigment: light tan to light purplish brown.

2. Glucose asparagine agar
Growth: moderate, pale brown to light purplish brown
Aerial mycelium: white to grayish blue.
Reverse: light brown to purplish brown.
Soluble pigment: light tan to light purplish brown.

3. Glycerin asparagine agar
Growth: moderate, pale brown to grayish brown.
Aerial mycelium: white to grayish blue.
Reverse: light brown to dark brown.
Soluble pigment: light tan to pale purple brown.

4. Starch agar
Growth: good, tan to light brown.
Aerial mycelium: abundant, white to light grayish blue.
Reverse: light brown to purplish brown.
Soluble pigment: colorless to light purplish brown.

5. Tyrosine agar
Growth: moderate, brown.
Aerial mycelium: sparse, white to gray.
Reverse: brown
Soluble pigment: blackish brown.

6. Nutrient agar
Growth: moderate, pale brown.
Aerial mycelium: sparse, white to grayish white.
Reverse: tan.
Soluble pigment: tan to pale brown.

7. Yeast malt agar
Growth: good, tan.
Aerial mycelium: abundant, cream to gray to light grayish blue.
Reverse: tan to orange brown.
Soluble pigment: light orange yellow to tan.

8. Oatmeal agar
Growth: good, pale brown to grayish brown.
Aerial mycelium: white to cream to light grayish blue.
Reverse: light brown to purplish brown.
Soluble pigment: light brown to purplish brown.

3. Physiological characteristics a. Growth temperature range (yeast malt agar, 2 weeks) —: no growth; +: moderate growth; ++: good growth; +++: abundant growth)

| | |
|---|---|
| 15° C | – ~ + |
| 20 | + |
| 24 | ++ |
| 28 | ++ ~ +++ |
| 30 | +++ |
| 32 | +++ |
| 37 | +++ |
| 40 | ++ ~ +++ |
| 45 | ++ |
| 55 | – |

F
It will be apparent from the above results that the growth temperature range of this strain is 15° to 45° C.

b. Liquefaction of gelatin: negative (24° C, 3 weeks).
c. Hydrolysis of starch: positive (weak).
d. Coagulation of skimmed milk: negative. Peptonization of skimmed milk: positive.
e. Production of melanoid pigments
Tyrosine agar: positive.
Peptone yeast extract iron agar: positive (weak).

4. Utilization of carbon sources (Pridham-Gottlieb medium)(+ growth, − no growth).

| | |
|---|---|
| a. L-Arabinose | + |
| b. D-Xylose | + |
| c. D-Glucose | + |
| d. D-Fructose | + |
| e. Sucrose | + |
| f. i-Inositol | + |
| g. L-Rhamnose | + |
| h. Raffinose | + |
| i. D-Mannitol | + |
| j. Control (no additive) | − |

The foregoing observed characteristics of Strain C-2801 indicate clearly that the strain belongs to the genus Streptomyces. Of the known species of Streptomyces, those which are more or less similar to the present strain include *Streptomyces afghaniensis* Shimo et al., *Streptomyces lanatus* Frommer, *Actinomyces coeruleorubidus* Preobrazhenskaya, *Actinomyces coerulatus* Krassilnikov et al. and *Actinomyces coeliatus* Krassilnikov et al. The characters of Strain C-2801 were compared with the original descriptions of the above similar microorganisms and with the descriptions in International Streptomyces Project (hereinafter referred to briefly as ISP). A comparative cultivation of ISP strains and the present strain using identical conditions was also performed.

The apparent differences between Strain C-2801 and the above-mentioned various microorganisms are as follows.

*Streptomyces afghaniensis*

The reverse side of its colony on yeast malt agar, starch agar or glycerol asparagine agar is orange-colored or reddish brown. The soluble pigment is also orange-colored or reddish brown.

*Streptomyces lanatus*

Spore chains are closed spirals. The reverse side of its colony on yeast malt agar, Starch agar, oatmeal agar or glycerol asparagine agar is colorless.

Light yellowish brown soluble pigments are produced on starch agar and oatmeal agar.

*Actinomyces coeruleorubidus*

The reverse side of its colony on starch agar of oatmeal agar is yellow to yellowish green. Reddish soluble pigments are produced on yeast malt agar, starch agar and glycerol asparagine agar.

*Actinomyces coerulatus*

Mature spore chains are long with more than 50 spores per chain. No soluble pigments are produced on yeast malt agar, starch agar, glycerol asparagine agar, oatmeal agar, etc.

*Actinomyces coeriatus*

Spore chains are closed spirals.

Brilliant blue to violet soluble pigments are produced in yeast malt agar, oatmeal agar, starch agar and glycerol asparagine agar.

of the Streptomyces microorganisms which are known to produce cephalosporin-group antibiotics, the following species appear to be comparatively similar to the present strain. *Streptomyces chartreusis* and *Streptomyces viridochromogenes* (Antimicrobial Agents and Chemotherapy 2, 122–131(1972)). Reference to the original descriptions of the two species, the ISP descriptions of them and the comparative cultivation of ISP strains and the present strain under the same conditions shed light on the following apparent differences.

*Streptomyces chartreusis*

A cream-colored aerial mycelium is produced on sucrose nitrate agar. The reverse side is yellow and the soluble pigment is yellow, too. A yellowish brown pigment is produced on an oatmeal agar and the reverse side of its colony on starch agar is greenish yellow. The aerial mycelium of open spiral is produced.

*Streptomyces viridochromogenes*

The aerial mycelium is open spiral. No distinctive soluble pigment is produced on any of sucrose nitrate agar, starch agar, oatmeal agar, etc. The reverse side of its colony on oatmeal agar, yeast malt agar or starch agar is grayish green to greenish brown.

The foregoing facts made it difficult to identify Strain C-2801 with any of the known species of the genus Streptomyces and, accordingly, the strain was considered to be a new species.

After the morphology of its aerial mycelium, this microorganism was named *Streptomyces heteromorphus*.

On the other hand, the various characteristics of Strain C-2878 and Strain C-2879 are given below. The cultural characteristics are those observed in the routine manner after 14 days of incubation at 28° C unless otherwise indicated.

1. Morphological characteristics (on glucose asparagine agar)

a. Strain C-2878

The aerial mycelium, with open or closed spore-bearing spores, arises monopodially from the well-branched vegatative mycelium.

The spores occur generally in chains, 10 or more spores per chain. The shape of the spore is ovoid or ellipsoidal (0.6 − 0.8 × 0.9 − 1.3 $\mu$), with a spiny surface. No other special organs are observed.

b. Strain C-2879

The characteristics of this strain are in agreement with the above described characters of Strain C-2878.

| (2) Cultural characteristics on various media | | | |
|---|---|---|---|
| Medium | | Strain C-2878 | Strain C-2879 |
| (1) Sucrose nitrate agar | G* | sparse, colorless to cream. | sparse to moderate, light tan to light grayish brown |
| | A | not formed | sparse(white or not formed |
| | R | colorless to light tan | light tan to light grayish brown |
| | S | colorless | colorless to light yellow |
| (2) Glucose asparagine agar | G | moderate, colorless to pale brown | moderate,pale light brown |
| | A | gray to bluish gray | white to grayish white to bluish gray |
| | R | dark tan | light tan to light brown |
| | S | Colorless to light tan | colorless to light yellow |
| (3) Glycerol asparagine agar | G | moderate, grayish brown to dark brown | moderate, tan |
| | A | white to grayish white | sparse, white to bluish white |
| | R | dark brown to dark greenish brown | tan |
| | S | light tan to light yellowish brown with greenish | yellow to gold |

(2) Cultural characteristics on various media -continued

| Medium | | Strain C-2878 | Strain C-2879 |
|---|---|---|---|
| (4) Starch agar | G | tinge moderate, light tan to pale light brown | good, colorless to cream |
| | A | gray to bluish gray | white to bluish gray |
| | R | light tan to pale light brown | colorless to light tan |
| | S | colorless | colorless |
| (5) Tyrosine agar | G | moderate, dark brown to blackish brown | moderate, dark brown |
| | A | sparse, white | sparse, white |
| | R | dark brown to blackish brown | blackish brown |
| | S | dark brown | blackish brown |
| (6) Nutrient agar | G | sparse, colorless to light tan | sparse, colorless to tan |
| | A | not produced | not produced |
| | R | light tan | pale brown |
| | S | colorless to tan | tan |
| (7) Yeast malt agar | G | moderate, colorless to light | good, pale light brown |
| | A | abundant, white to bluish white | white to bluish gray |
| | R | tan | light brown |
| | S | colorless to tan | orange tan to yellowish light brown |
| (8) Oatmeal agar | G | good, colorless to pale light brown | good, pale light brown to pale brown |
| | A | white to grayish blue | grayish white to bluish gray |
| | R | light brown to greenish brown | dark tan to light brown |
| | S | colorless to pale light brown | pale light brown |

*G-growth; A-aerial mycelium; R-reverse; S-soluble pigment. All data are based on incubation at 28° C for 14 days.

3. Physiological properties a. Growth temperature range (2 weeks on glucose asparagine agar) (− no growth; + growth, ++ good growth; +++ abundant growth)

| | Strain C-2878 | Strain C-2879 |
|---|---|---|
| 15° C | − ∼ + | − ∼ + |
| 20° C | + | + |
| 24° C | ++ | ++ |
| 28° C | +++ | +++ |
| 30° C | +++ | +++ |
| 32° C | +++ | +++ |
| 37° C | +++ | +++ |
| 40° C | ++ | ++ |
| 45° C | ++ | ++ |
| 55° C | − | − |

It is apparent from the above results that the strain grows over the temperature range of 15° to 45° C.

| | Strain C-2878 | Strain C-2879 |
|---|---|---|
| a. Liquefaction of gelatin | Positive | Positive |
| b. Hydrolysis of starch | Positive (weak) | Positive (weak) |
| c. Coagulation of skimmed milk | Negative | Negative |
| Peptonization of skimmed milk | Positive | Positive |
| d. Production of melanoid pigments | | |
| Tyrosine agar | Positive | Positive |
| Peptone yeast extract iron agar | Positive | Positive |

4. Utilization of carbon sources (Pridham and Gottlieb medium) (+ growth; ± suspected growth; − no growth)

| | Strain C-2878 | Strain C-2879 |
|---|---|---|
| i-Inositol | + | + |
| D-Mannit | + | + |
| D-Xylose | + | + |
| L-Arabinose | − ∼ ± | − ∼ ± |
| D-Glucose | + | + |
| D-Fructose | − | − |
| L-Rhamnose | + | + |
| Sucrose | + | + |
| Raffinose | + | + |
| Control | − | − |

From the above characteristics, it is obvious that both Strain C-2878 and Strain C-2879 belong to the genus Streptomyces. As to their relationship, it can be fairly concluded that these strains are of the same species, for excepting their apparent differences in the reverse colors of growth on glucose asparagine agar and on glycerol asparagine agar as well as in the color of soluble pigment, these strains are in good agreement with each other in morphological, cultural and physiological characteristics. These findings, coupled with the observed amoumts of aerial mycelium produced, suggest that Strain C-2879 is a spontaneous mutant of Strain C-2878.

An attempt was made to compare Strain C-2878 to known species of the genus Streptomyces and particularly to the producers of bluish aerial mycelia.

It was found that the described character on glucose asparagine agar of *Streptomyces viridochromogenes*, which is a typical species producing a bluish-colored aerial mycelium (S.A. Waksman, The Actinomycetes II, 287), bears a fair resemblance to the corresponding character of the present strains comparative cultivation test was performed on the present strain (Strain C-2878) and *Streptomyces viridochromogenes* under the same conditions. The test shed light on some prominent differences between the two microorganisms, i.e., their characteristics on sucrose nitrate agar, yeast malt agar, oatmeal agar and other media, their different propensities to produce melanoid pigments, and their different abilities to assimilate carbon sources, among other aspects.

As the species which are able to produce some cephalosporin-group antibiotic or other, and which possess bluish aerial mycelia, there are known *Streptomyces chartreusis* and *Streptomyces heteromorphus* which is a new species within the purview of this application. However, neither of these microorganisms is like Strain C-2878.

It was concluded from the foregoing obversations that both Strain C-2878 and Strain C-2879 belong to a novel species which cannot be relegated to any of the known species of the genus Streptomyces and, accordingly, there was assigned to them a specific name of *Streptomyces panayensis* after Panay Island of the Republic of the Philippines where soil samples containing them had been collected.

Of course, it is well known that characteristics of actinomycetes and particularly of microorganisms of the genus Streptomyces are not constant but subject ot mutational changes, both spontaneous and induced. The antibiotic C-2801-X-producing strains belonging to the genus Streptomyces are no exceptions. For instance, they can be easily caused to undergo mutation by artificial mutagenic treatments such as irradiation with ultraviolet ray, X-rays or other radiation or by treatment with chemicals (e.g., sodium nitrite, N-methyl-N'-nitro-N-nitrosoguanidine, etc.), and such mutants can all be employed for the purposes of this invention inasmuch as they are able to elaborate antibiotic C-2801-X.

The above exemplified strains are deposited with the following accession numbers:

*Streptomyces heteromorphus* C-2801(IFO-13575, FERM P-No. 2271, ATCC-31054)
*Streptomyces panayensis* C-2878(IFO-13576, FERM P-No. 2272, ATCC-31055)
*Streptomyces panayensis* C-2879(IFO-13577, FERM P-No. 2273, ATCC-31056)

The numbers in the parenthesis indicated by IFO, FERO and ATCC are the accession numbers at Institute for Fermentation, Osaka, Japan (IFO); The fermentation Research Institute of the Agency of Industrial Science and Technology, Japan (FERM); and American Type Culture Collection, U.S.A. (ATCC), respectively.

In accordance with this invention, such an antibiotic C-2801-X-producing strain is cultivated in a culture medium. The medium may be a fluid medium or a solid medium, although a fluid medium is more advantageous. In the medium is incorporated the nutrient sources which are conventionally employed for the cultivation of a microorganism of the Streptomyces organisms, such as sources of carbon and nitrogen, etc. As the sources of carbon, there may be mentioned, among others, glucose, starch, glycerol, dextrin, sucrose, millet jelly, molasses, lactose, maltose, etc. The nitrogen sources may, for example, be soybean meal, corn steep liquor, wheat bran, cotton seed meal, meat extract, rice bran, urea, ammonium salt (e.g., ammonium sulfate, ammonium nitrate, etc.) and other inorganic and organic nitrogenous compounds. As inorganic salts, there may be incorporated calcium carbonate, sodium chloride, calcium chloride, calcium phosphate, etc. It is also possible to incorporate other or-/and inorganic compounds which will help the microorganism to grow and promote its elaboration of the antibiotic C-2801-X.

As to the cultural methods empolyable, fluid culture, particularly submerged culture, is preferred. The cultivation is carried out under aerobic conditions. The cultivation pH may range from pH 5 to 9 and, preferably, from pH 6 to 8, the incubation temperature may range from 20° C to 40° C and, preferably, from 24° to 37° C, and the incubation time is somewhere between 20 and 240 hours and, preferably, between 24 and 120 hours.

Antibiotic C-2801-X thus produced in the broth can be harvested with advantage by procedures which, per se, are routinely employed. Antibiotic C-2801-X, being one of the so-called cephalosporin antibiotics, is a water-soluble amphoteric substance which is unstable under strongly acidic and under alkaline conditions and can be separated and recovered by various procedures taking advantage of the distinct acid and alkaline functionalities of its side chains. For example, there can be employed, either alone, in combination or in repetition, such procedures as the procedure which takes advantage of its distinct adsorptive affinity for nonionic adsorbent resins such as non-ionic polystryene-type adsorbent resins [e.g., Amberlite XAD-2 (manufactured by Rohm and Hass Co., U.S.A.), Diaion HP-10 (Manufactured by Mitsubishi Chemical Industries, Ltd., Japan)]; the procedure which takes advantage of the basicity of basic functional group, using cation-exchange resins [e.g., Dowex 50W (Dow Chemicals, U.S.A.)]; the procedure which take advantage of the acidity of acidic functional group, using anion-exchange resins [e.g. Amberlite IRA-68 (manufactured by Rohm and Hass Co., U.S.A.)] or anion-exchange cellulose [e.g., DEAE(diethylaminoethyl)-cellulose (manufactured by Siekagaku Kogyo, Ltd., Japan)].

Since the antibiotic produced in the described manner is unstable under strongly acid conditions as well as under alkaline conditions, it is preferable to use neutral solvents or buffers adjusted to a pH range suitable for stabilization of the antibiotics in the separation and recovery process. And in carrying out elutions from adsorbents or ion exchangers, it is advisable, in order that the separation of components may be effected with some precision, to mix a water-miscible organic solvent, such as a lower ketone (e.g., acetone, methyl ethyl ketone) or lower aliphatic alcohol (e.g., methanol, ethanol, propanol), with water or a buffer solution and to vary the concentration of solvents, or the salt concentration of the buffer continually or stepwise.

The following are the properties of antibiotic C-2801-X monosodium salt as obtained in Example 1.

(Physical and Chemical properties)

1. Shape and color: Yellowish white powders
2. Elemental analysis:

|   | Found | Calculated |
|---|-------|------------|
| C | 48.46 | 48.62 |
| H | 4.85  | 4.57 |
| N | 6.98  | 6.79 |
| S | 5.13  | 5.19 |

Figure 2:
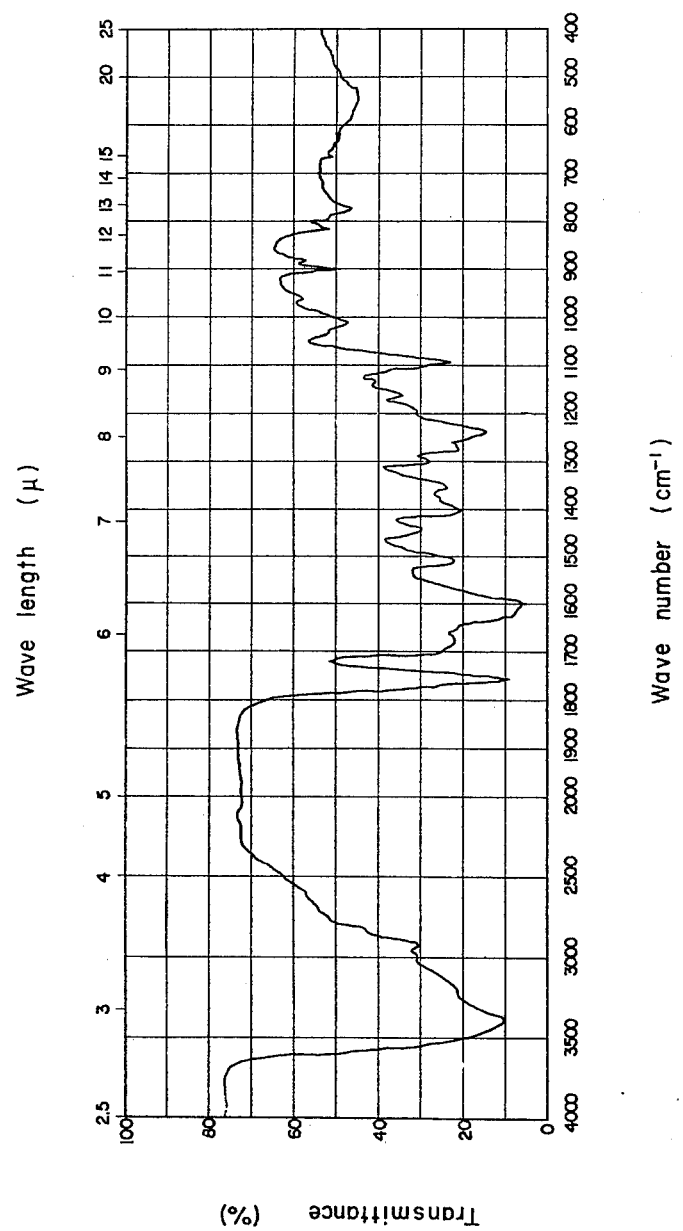

3. Molecular formula: $C_{25}H_{28}N_3O_{12}SNa$
4. Optical rotation: $[\alpha]_a^{25°}$ (c=0.5 in water) + 124.4°
5. UV absorption: (FIG. 1)
    Maxima $\lambda_{max}^{H_2O}(E_{1cm}^{1}\%)$; 235 μ (208), 318 μ (274)
    Shoulder; 295 μ ($E_{1cm}^{1}\%$ 255)
6. IR spectrum (KBr):(FIG. 2)
    Characteristic wave numbers (cm$^{-1}$) of IR absorption of Antibiotic C-2801-X (monosodium salt) are as follows:
    3400 (S), 3200 (S), 3000 (M), 2920 (M), 1760 (S), 1690 (M), 1630 (S), 1600 (S), 1510 (M), 1440 (M), 1400 (M), 1350 (M), 1300 (M), 1275 (M), 1240 (S), 1165 (W), 1140 (W), 1110 (W), 1095 (M), 1010 (W). S: strong, M: medium, W: weak
7. Solubility: Soluble in water, methanol and ethanol. Insoluble in ethyl acetate, chloroform and ether.
8. Color reactions: Ninhydrine reaction: + Barton's reaction (using a mixture, as a reagent, of equal volume of 1 % aqueous ferric chloride $FeCl_3$) and 1 % aqueous potassium ferricyanide $\{K_3Fe(CN)_6\}$: +
9. Acidity-alkalinity: Amphoteric
10. Paper chromatography (Whatman filter paper No. 1, manufactured by Balston Ltd., Great Britian)

Rf values:
n-Butanol-acetic acid-water        0.12

| -continued | |
|---|---|
| (4:1:5) | |
| n-Butanol-acetic acid-water | 0.42 |
| (2:1:1) | |
| 70 % Isopropanol | 0.33 |

Based on the above physical and chemical properties as well as the results of other analyses, the chemical structure of this new antibiotic C-2801-X was determined as follows.

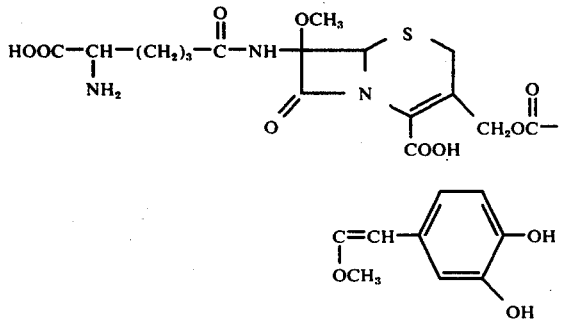

11. Antimicrobial spectrum:
    Medium: Tripticase Soy Agar (BBL) (manufactured by Becton Dickenson Co., U.S.A.), pH 6.5, minimal inhibitory concentrations mcg/ml., temperature 37° C

| Test organisms | |
|---|---|
| Staphylococcus aureus 209 P | 50 |
| Staphylococcus aureus 209 P (chloramphenicol, streptomycin, tetracycline and erythromycin-resistant) | 50 |
| Straphylococcus aureus No.87 | 50 |
| Bacillus subtilis PCI 219 | 12.5 |
| Bacillus pumilus IFO-3813 | 50 |
| Escherichia coli NIHJ | 50 |
| Escherichia coli (clinical isolate, antibiotic-susceptible strain) | 25 |
| Escherichia coli (clinical isolate*) | 25 |
| Escherichia coli (clinical isolate**) | 25 |
| Proteus vulgaris IFO-3988 | 12.5 |
| Proteus mirabilis IFO-3849 | 3.13 |
| Proteus morganii IFO-3848 | 25 |
| Klebsiella pneumoniae IFO-3512 | 6.25 |
| Pseudomonas aeruginosa IFO-3080 | >100 |
| Pseudomonas aeruginosa NCTC-10490 | >100 |
| Salmonella typhimurium IFO-12529 | 6.25 |
| Salmonella enteritidis IFO-3313 | 6.25 |
| Aerobacter cloacae IFO-12009 | 25 |
| Alcaligenes faecalis IFO-13111 | 12.5 |

*The strain is resistant to tetracycline, streptomycin, kanamycin, lividomycin, aminobenzylpenicillin and sulbenicillin.
**The strain is resistant to sulfonamide, streptomycin and sulbenicillin.
(The IFO-numbers given above are the accession numbers at the Institute for Fermentation, Osaka, Japan).

12. Acute toxicity:

In an acute toxicity test in mice, there occurred no death when 400 mg. of Antibiotic C-2801-X monosodium salt per kilogram of body weight was administered intravenously.

Antibiotic C-2801-X which can be obtained by this invention can also be recovered as salts, for example, alkali metal salts (e.g., nono- and disodium salts, mono- and dipotassium salts), monoammonium salt, and various inorganic and organic acid salts (e.g., hydrochloride, sulfate, alkylsulfonate, etc.), and the free compound and a salt thereof can be interchanged by per se known procedures.

In the present specification, the wording "Antibiotic C-2801-X" includes both free form and salts of the antibiotic C-2801-X, unless otherwise noted.

The resultant antibiotic C-2801-X and its salts inhibit the growth of Staphylococcus aureaus, Bacillus subtilis, Escherichia coli, Proteus vulgaris, Salmonella typhimurium, aerobic bacteria, etc. Therefore, the antibiotic C-2801-X and its salts are used as an agent for the treatment of mammals including human beings suffering from urinary tract infections (e.g., cystitis, nepropyelitis, etc.), respiratory tract infections (e.g., bronchitis, pneumonia, etc.), colitis, septicemia, purulent diseases, etc. In the treatment of such diseases in human beings, Antibiotic C-2801-X or a salt thereof can be administered at the regular daily dosage of 1 to 2 grams per adult in admixture with a pharmacologically acceptable inert excipient in such dosage forms as parenteral injections, etc. Dosage of C-2801-X when administered to other hosts may be determined in proportion to their body weights as in human beings. A typical dosage form is indicated below. Injection (per one administration)

In 2 ml. of distilled water is dissolved a 500 mg. equivalent of Antibiotic C-2801-X monosodium salt and, after aseptical filtration, the solution is dispensed into sterilized vials and freeze-dried.

To inject, the above powder is dissolved in 2 ml. of distilled water for injection and the solution is administered intramuscularly. In the case of adult humans, injections are performed every 6 to 8 hours.

Capsule:
A capsule is prepared so as to contain 550 mg. of graules consisting of the following components.

| | |
|---|---|
| Antibiotic C-2801-X monosodium salt | 500 mg. |
| Lactose | 20 mg. |
| Starch | 20 mg. |
| Magnesium stearate | 10 mg. |
| | 550 mg. |

In the case of adult human, one capsule is administered every 6 hours.

As Antibiotic C-2801-X has a broad antimicrobial spectrum, it can be used as a disinfectant as well as a preservative, the disinfectant activity being utilizable for instance in asepticizing the air and utensils, and the like, e.g., in hospital rooms, in such a manner as by spraying the air and the utensils with an effective quantity of, e.g., ethanolic solution of the antibiotic.

For further detailed explanation of the invention, the following examples are given, wherein the term "part(s)" means "weight part(s)," unless otherwise noted and the relationship between "part(s)" and "part(s) by volume" corresponds to that between "gram(s)" and "milliliter(s)."

EXAMPLE 1

A fermenter of 2,000 parts by volume capacity is filled with 500 parts by volume of a medium composed of 2 % of glucose, 3 % of soluble starch, 1 % of corn steep liquor, 1 % of soybean meal, 0.5 % of peptone, 0.3 % of sodium chloride and 0.5 % of CaCO₃ (pH 7.0) and sterilized at 120° C for 30 minutes.

The fermenter is inoculated with *Streptomyces heteromorphus* C-F2801 (ATCC-31054, FERM P-No.2271) and incubated at 28° C for 40 hours. The resultant seed culture is transferred to a fermenter of 50,000 parts by volume capacity containing 30,000 parts by volume of a medium of the same composition as above and cultivated at 28° C under aeration and agitation for 24 hours (aeration 100 %, agitation 280r.p.m.).

A 10,000 parts by volume portion of the resultant culture is further transferred to a fermenter of 200,000 parts by volume capacity containing 100,000 parts by volume of a medium containing 3 % of sucrose, 2 % of Proflo (defatted and cooked cotton seed flour),- (manufactured by Traders Oil Mill Company, U.S.A.), 1 % of corn steep liquor, 0.05 % of $FeSO_4$, 0.5 % of $K_2HPO_4$, 0.3 % of sodium chloride and 0.5 % of $CaCO_3$ (pH 7.0) and incubated at 28° C under aeration (100 %) and agitation (200 r.p.m.) for 66 hours.

The resultant culture broth, amounting to 93,000 parts by volume, is adjusted to a pH 5 with 10 % phosphoric acid and stirred with Hyflo-Supercel (filter aid; manufactured by Johns Manville Products, U.S.A.).

The mixture is subjected to a filter press to obtain 80,000 parts by volume of a filtrate. This filtrate is passed through a column of 8,000 parts by volume of Amberlite XAD-2 at the flow rate of 16,000 parts by volume per hour. The resin which has now adsorbed the active substance is washed with 16,000 parts by volume of 1/15 mole phosphate buffer (pH 6.5)- methanol (9:1) and, then, the antibiotic is eluted with 16,000 parts by volume of 1/15 mole phosphate buffer (pH 6.5)-methanol (4:1), the eluate being fractionated into 4,000 parts by volume portions. The 2nd to 4th fractions contain Antibiotic C-2801-X. The column is further eluted with 16,000 parts by volume of 1.15 mole phosphate buffer (pH 6.5)-methanol (1:1), the eluate again being fractionated into 4,000 parts by volume portions. The 1st and 2nd fractions contain Antibiotic C-2801-X.

The thus-obtained fractions containing Antibiotic C-2801-X, amounting to a total of 20,000 parts by volume, are pooled and diluted with 60,000 parts by volume of 1/15 mole phosphate buffer (pH 5.6) and the diluted solution is passed columnwise through 2,000 parts by volume of Amberlite XAD-2 at the rate of 4,000 parts by volume per hour. The resin which has adsorbed the active substance is washed with 1,000 parts by volume of 1/15 mole phosphate buffer (pH 5.6) and, then, irrigated with 2,000 parts by volume of water and 4,000 parts by volume of 10 % aqueous ethanol in the order mentioned. The effluent is fractionated into 500 parts by volume portions to obtain fractions No.1 to No.12.

Each of these fractions is analyzed by ascending paper chromatography (Whatman No.1) with a developing solvent mixture of n-butanol-acetic acid-water (2:1:1). The papergram was subjected to bioautography against *Bacillus subtilis* and *Proteus vulgaris* as test organisms. The inhibition spot indicates that antibiotic C-2801-X is contained in fractions No. 6 through No.10.

The thus-obtained fractions, amounting to 2,500 parts by voluem, which contain Antibiotic C-2801-X are passed through a column packed with 250 parts by volume of Dowex 50 W×4(100–200 mesh) equilibrated beforehand with 1/10 mole sodium acetate buffer (pH 4.4) at the flow rate of 250 parts by volume per hour, whereby the active substance is adsorbed. Then, the resin is washed with 10 % aqueous ethanol. The column is further eluted with a solvent system of 1/10 mole acetic acid-sodium acetate buffer (pH 4.4)-ethanol (9:1) and the active fractions are collected. These fractions are then charged to a column packed with 200 parts by volume of Amberlite XAD-2 to adsorb the active substance and, then, 1/15 mole phosphate buffer of pH 5.6 is passed until the pH of the effluent is 5.6. The column is washed with water and eluted with 10 % aqueous ethanol. The eluate, 100 parts by volume, which shows the antimicrobial activity, is concentrated under reduced pressure at a temperature not exceeding 15° C to remove the ethanol and the resulting aqueous solution is freeze-dried. The procedure give 2.5 parts of crude powders of Antibiotic C-2801-X monosodium salt (Purity: 75 %).

One part of thus-obtained crude powders of Antibiotic C-2801-X (monosodium salt) is dissolved in 10 parts by volume of an aqueous solution which has been prepared by dissolving sodium chloride in 1/10 mole sodium acetate buffer of pH 4.4 to give a concentration of 1/10 mole. The resultant solution is run onto a column packed with DEAE-cellulose (chloride-form). The column is developed with the same solution as above and the active fractions are collected. These fractions are further passed through a column packed with Amberlite XAD-2, whereby the active substance is adsorbed. The column is washed with 1/15 mole phosphate buffer of pH 5.6 until the pH of the effluent is 5.6 and, then, washed with 500 parts by volume of water. Elution is carried out with 5 % aqueous ethanol and the fractions which give positive ninhydrin and Barton's reactions are combined, concentrated under reduced pressure and freeze-dried. The above procedure gives 0.550 part of a pure preparation of Antibiotic C-2801-X (monosodium salt).

To 1 part of the crude Antibiotic C-2801-X powders obtained above is added 10 parts of cellulose powder (manufactured by Toyo Roshi, Ltd., Japan), and the mixture, after stirring, is placed on top of a column of cellulose powder previously packed with the upper layer of n-butanol-acetic acid-water (4:1-5). A small amount of the solvent is added and, after stirring with caution so that the column top will not be disturbed, the column is developed with the above-mentioned solvent.

The fractions which give positive ninhydrin and Barton's reactions are diluted with water and concentrated under reduced pressure.

After removal of the butanol by distillation, the residual aqueous solution is run into a column packed with Amberlite XAD-2, followed by passage of 1/15 mole phosphate buffer of pH 5.6 until the pH of the effluent is 5.6. The column is then washed with 500 parts by volume of water.

Elution is performed with 5 % ethanol and the fractions giving positive ninhydrin and Barton's reactions are collected, concentrated under reduced pressure and freeze-dried. The described procedure gives 0.400 part of pure Antibiotic C-2801-X (monosodium salt).

EXAMPLE 2

A fermenter of 2,000 parts by volume capacity is filled with 500 parts by volume of a culture medium (pH 7.0) composed of 2 % of glucose, 3 % of soluble starch, 1 % of corn steep liquor, 1 % of soybean meal, 0.5 % of peptone, 0.3 % of sodium chloride and 0.5 % of CaCO₃, and sterilized at 120° C for 30 minutes.

The fermenter is then inoculated with *Streptomyces panayensis* C-2878(ATCC-31055,FERM-2272) and incubated at 28° C for 40 hours. The resultant seed culture is transferred to a 50,000 parts by volume fermentor containing 30,000 parts by volume of a fermentation medium (pH 7.0) composed of 1 % of glycerol, 2 % of glucose, 2 % of soluble starch, 1 % of soybean meal, 1 % of cotton seed meal, 1 % of corn steep liquor, 0.5 % of peptone, 0.5 % of sodium chloride and 0.5 % of CaCO₃ and incubation under aeration and agitation is carried out at 28° C for 66 hours (100 % aeration, 280 r.p.m.). The production of the antibiotic is maximal in 54 to 66 hours.

From 28,000 parts by volume of thus-obtained broth, there is obtained 25,000 parts by volume of filtered broth in the same manner as in Example 1.

This filtrate is passed through a column of 2,500 parts by volume of Amberlite XAD-2 to adsorb the active substance, followed by washing with 5,000 parts by volume of water. Elution is performed with 50 % aqueous methanol and the eluate is obtained is concentrated under reduced pressure, whereby about 2,000 parts by volume of a solution containing C-2801-X is obtained. One thousand parts by volume of this solution is run onto a column of 300 parts by volume of Amberlite XAD-2 and, then, 1/15 mole phosphate buffer of pH 6.5 is passed through the column until the pH of the effluent is 6.5. To desorb the C-2801-X, use is made of a developing solvent system using a mixture of methanol and 1/15 mole phosphate buffer of pH 6.5, in which the concentration of methanol is continually increased from 10 % to 50 %. In this process C-2801-X emerges in the fractions corresponding to 28 % to 35 % methanol. To 300 parts by volume of thus-obtained C-2801-X-rich fractions are added 900 parts by volume of 1/15 mole phosphate buffer of pH 5.6 and the mixture is passed column-wise over 100 parts by volume of Amberlite XAD-2, whereupon, the active substance is adsorbed on the resin. The column is washed with water and elution is carried out with 10 % aqueous ethanol. The active fractions are concentrated under reduced pressure and freeze-dried. The described procedure gives 1 part of crude powders of Antibiotic C-2801-X monosodium salt. (Purity 35 %).

One thousand parts by volume of the solution containing C-2801-X which is obtainable as above is passed down a column packed with 200 parts by volume of DEAE-cellulose (chloride-form). the cellulose is washed with 0.3 % of aqueous acetic acid and, then, elution is performed with 0.1 mole aqueous sodium chloride containing 0.3 % of acetic acid, whereby C-2801-X is desorbed. The C-2801-X fractions are pooled and passed columnwise over 100 parts by volume of Amberlite XAD-2 to adsorb the active substance and after the column is washed with water, elution is performed with 50 % aqueous methanol. The active fractions are concentrated and freeze-dried. The procedure give 1 part of crude powders of C-2801-X (monosodium salt). Purity 35 %. Two parts of crude C-2801-X powders thus are obtained are further purified by the same purification procedure as set forth in Example 1, whereupon 0.363 part of a pure preparation of C-2801-X (monosodium salt) is obtained.

EXAMPLE 3

A fermenter of 2,000 parts by volume capacity is filled with 500 parts by volume of a culture medium (pH 7.0) composed of 2 % of glucose, 3 % of soluble starch, 1 % of corn steep liquor, 1 % of soybean meal, 0.5 % of peptone, 0.3 % of sodium chloride and 0.5 % of CaCO₃ and, then, sterilized at 120° C for 30 minutes. The fermenter is then inoculated with *Streptomyces panayensis* C-2879 (ATCC-31056,FERM P-No.2273) and incubated at 28° C for 40 hours. The resultant seed culture is transferred to a 50,000 parts by volume fermenter containing 30,000 parts by volume of a medium of the same composition as above and incubated at 28° C under aeration and agitation for 24 hours (100 % aeration, 280 r.p.m.). Then, a 10,000 parts by volume portion of the culture is further transferred to a 200,000 parts by volume fermenter containing 100,000 parts by volume of a fermentation medium (pH 7.0) composed of 3 % of sucrose, 2 % of Proflo, 1 % of corn steep liquor, 0.05 % of FeSO₄, 0.05 % of K₂HPO₄, 0.3 % of sodium chloride and 0.5 % of CaCO₃ and incubated at 28° C under aeration and agitation (100 % aeration; 200 r.p.m.) for 66 hours. A 95,000 parts by volume portion of the resultant broth is subjected to the same separation and purification procedures as set forth in Example 1 to obtain 2.25 parts of crude powders of Antibiotic C-2801-X (monosodium salt). This product is further subjected to separation and purification procedures as in Example 1 to obtain 1.45 part of a pure preparation of Antibiotic C-2801-. (monosodium salt).

What we claim is:
1. A compound selected from the group consisting of a compound of the formula:

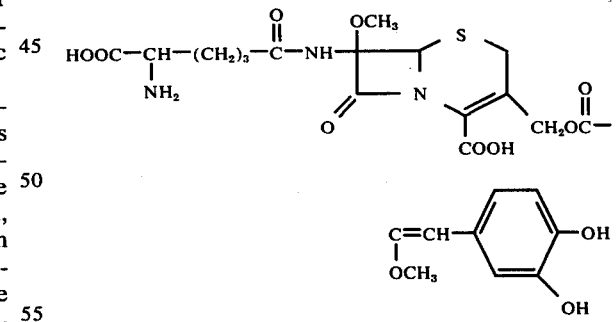

and pharmaceutically acceptable salts thereon.

* * * * *